United States Patent [19]

Tucker

[11] 4,221,219

[45] Sep. 9, 1980

[54] IMPLANTABLE INFUSION APPARATUS AND METHOD

[75] Inventor: Elton M. Tucker, Medfield, Mass.

[73] Assignee: Metal Bellows Corporation, Sharon, Mass.

[21] Appl. No.: 929,427

[22] Filed: Jul. 31, 1978

[51] Int. Cl.³ .............................................. A61M 7/00
[52] U.S. Cl. ................................................. 128/260
[58] Field of Search .................. 128/1 R, 172, 213 R, 128/214 F, 232, 260, 268, DIG. 12; 3/1 R

[56] References Cited

U.S. PATENT DOCUMENTS

| | | | |
|---|---|---|---|
| 3,527,220 | 9/1970 | Summers | 128/260 |
| 3,840,009 | 10/1974 | Michaels et al. | 128/272 |
| 3,923,060 | 2/1975 | Ellinwood, Jr. | 128/214 F |
| 4,013,074 | 3/1977 | Siposs | 128/214 F |
| 4,056,095 | 11/1977 | Rey et al. | 128/260 |
| 4,077,405 | 3/1978 | Haerten et al. | 128/214 F |
| 4,137,913 | 2/1979 | Georgi | 128/214 F |
| 4,146,029 | 3/1979 | Ellinwood, Jr. | 128/260 |

*Primary Examiner*—C. Fred Rosenbaum
*Attorney, Agent, or Firm*—Cesari & McKenna

[57] ABSTRACT

Implantable infusion apparatus has a main infusate reservoir and a smaller volume auxiliary infusate reservoir interconnected by a passage. Fail-safe electrical valve means controls infusate flow from the main reservoir to the auxiliary reservoir and from the auxiliary reservoir exteriorly of the apparatus so as to prevent infusate overdose in the event of valve failure.

9 Claims, 2 Drawing Figures

IMPLANTABLE INFUSION APPARATUS AND METHOD

This invention relates to an infusion method and to infusion apparatus that can be implanted in a body to dispense infusate at a selected site in the body for a prolonged period. It relates more particularly to apparatus of this type which can be refilled and recharged periodically by subcutaneous injection through a septum mounted in the apparatus and located under the skin.

BACKGROUND OF THE INVENTION

The implanting of prosthetic devices such as infusion apparatus or pumps in the body is a relatively recent development. These devices are used to dispense infusate such as hormones or chemicals, for example, into the body to alleviate a particular physiological problem of the patient.

Usually such pumps include a housing made of a material such as titanium that is compatible with the physiological system. The housing defines a cavity divided by a movable wall such as a bellows capsule having one end secured to a housing wall, its opposite end being enclosed. The capsule thus divides the cavity into a pair of chambers whose volumes may be varied reciprocally by extending or compressing the bellows capsule. The chamber inside the bellows capsule is filled with infusate while the chamber defined by the outside of the bellows capsule and the housing wall is filled with a two-phase fluid such as chloroethane which has a significant vapor pressure at body temperatures. As it vaporizes, the fluid compresses the bellows capsule and forces the infusate therein through an outlet conduit leading to the infusion site.

The bellows capsule can be refilled periodically by injecting infusate through a penetrable septum located in the housing wall and leading to the interior of the bellows capsule. In the process of refilling and therefore expanding the bellows capsule, the two-phase fluid is pressurized condensing some of the gas, returning it to its liquid phase. Whereupon the liquid again commences to vaporize and compress the bellows capsule which thereupon dispenses the new charge of infusate. The rate of infusate flow is controlled by a flow restrictor in the outlet from the bellows capsule which is usually simply a length of capillary tubing. Examples of such infusion devices and their usage are described in detail in U.S. Pat. Nos. 3,731,681 and 3,951,147.

In some cases, the flow of infusate from the bellows capsule being compressed by the two-phase fluid is controlled more closely by means of an electrical valve located in the outlet from the bellows capsule. The opening and closing of the valve is controlled by a programmable controller which issues electrical pulses with a selected repetition rate or pulse duration which open and close the valve so that the apparatus dispenses infusate at a programmed rate which may vary with time or in response to changing conditions in the body such as temperature, sugar level, blood pressure or the like. An example of a programmable implantable pump of this general type is described in U.S. Pat. No. 4,077,405.

One problem with the prior infusion apparatus of the type described in the last mentioned patent is the potential for infusate overdose due to valve failure. In other words, the valve controlling the flow of infusate from the reservoir to the infusion site is invariably a normally closed valve which is opened when energized by signals from the controller. Therefore, if the valve fails in its open position (power continuously on), infusate will flow continuously from the collapsing infusate reservoir to the body site rather than at the programmed intervals and durations scheduled by the controller. In this event, there is a risk that the patient will receive an overdose of infusate which might cause a serious health hazard.

Another problem with the prior prosthetic devices of this general type stems from the fact that the flow rate of the infusate from the bellows capsule varies as the pressure of the two-phase fluid acting upon the capsule varies. That fluid pressure, on the other hand, changes as the patient's body temperature changes. Thus if the patient has a fever, the increased temperature causes the two-phase fluid to exert a greater pressure on the bellows capsule than is the case if the patient has a normal temperature thereby resulting in increased infusate flow. A change in atmospheric pressure will likewise change the infusate flow.

As is described in the last mentioned patent, this flow variation caused by temperature change can be compensated for by sensing the pressure of the two-phase fluid by means of a transducer exposed to that pressure and applying the signals from the transducer to the controller to change the repetition rate or pulse duration of the signals applied to the valve. However, the cost of the transducer and its connections to the controller increase the overall cost of the apparatus. Moreover, this means that the apparatus must include another dynamic part which itself can fail in such a way as to cause either an excess of flow or inadequate flow. In this connection, it should be emphasized that it is intended that infusion apparatus of the type with which we are concerned here remain implanted in the human body for a prolonged period, in the order of eight or ten years or more. Therefore it is essential that the apparatus contain as few dynamic parts as possible, those few parts being of unusually sturdy and rugged construction so that they are not prone to failure and when failed, fail in such a manner as to stop the infusion process. The addition of a pressure transducer to monitor the pressure of the two-phase fluid driving the bellows capsule is not consistent with that overall philosophy.

Finally, apparatus of this type sometimes should provide a uniform basal infusion flow to the patient over the long term which flow is supplemented at selected times by relatively short term bolus infusate doses. The last mentioned patent discloses various ways of accomplishing that objective. In one apparatus, infusate flows continuously from a main chamber to provide the basal needs of the patient. The bolus dose is provided by way of a separate flow path having a pulsed electrical valve and extending from the main chamber in parallel with the basal flow path. As discussed in the second mentioned patent, because of the very small basal flow rates required, it is quite difficult to make reliable flow restrictors whose orifices are small enough to provide such small flows. Also the small restriction orifices are prone to blockage.

In another variation of that patented apparatus, the basal and bolus flows are provided via a single valved fluid path, the valve being pulsed differently to achieve the different basal and bolus flow rates. Providing the basal flow in this manner requires that the valve be pulsed substantially continuously. Therefore, the valve consumes a relatively large amount of power requiring relatively frequent replacement of the battery that powers the valve.

SUMMARY OF THE INVENTION

Accordingly, the present invention aims to provide an implanted prosthetic device in the nature of infusion apparatus which eliminates the possibility of infusate overdose because of the failure of the valve or caridac failures of the control circuit controlling the flow of infusate from the infusate reservoir to the infusion site.

Another object of the invention is to provide apparatus of this type which has a minimum number of dynamic parts which are not prone to failure and do not contain sliding interfaces.

Another object is to provide an infusion method that achieves close control over infusate dosage over the long term.

A further object of the invention is to provide implantable infusion apparatus whose outlet flow rate is unaffected by changes in body temperature or ambient pressure.

Still another object of the invention is to provide implantable infusion apparatus which can remain implanted in a body for a prolonged period of time, being refilled and recharged by percutaneous injection of fresh infusate.

Yet another object is to provide such apparatus which can provide a uniform basal dose of infusate over a long term without consuming a large amount of electrical power.

Other objects will, in part, be obvious and will, in part, appear hereinafter. The invention accordingly comprises the sequence of steps and the features of construction, combination of elements and arrangement of parts which will be exemplified in the following detailed description, and the scope of the invention will be indicated in the claims.

Briefly the present infusion apparatus includes the usual housing containing an infusate reservoir preferably in the form of a bellows capsule situated in a housing chamber filled with a two-phase fluid which tends to expand at body temperature and compress the bellows. The apparatus may be refilled and recharged periodically by injecting fresh infusate through a septum located in the housing wall as described in detail in the aforesaid patents.

An outlet passage leads from the main bellows capsule to a second chamber within the housing with the end of the passage inside the second chamber being shaped to function as a valve seat. A second passage having one end located in the second chamber, also shaped to function as a valve seat extends through the housing wall and is connected to a capillary tube whose opposite end communicates with a catheter which is placed at the selected infusion site within the body.

Both the first and second passages are valved preferably but not necessarily, by a single valve member which is movably supported between the two valve seats. The member is movable between a first position wherein it engages the first valve seat interrupting flow of infusate from the main bellows capsule to the second chamber but permitting infusate flow out of the second chamber and a second position wherein it engages the second valve seat thereby permitting infusate flow from the main capsule into the second chamber, but preventing flow of infusate from the second chamber to the catheter. The valve member is normally biased against the first valve seat and is moved to its second position against the second valve seat by a solenoid which is energized by signals from a programmable controller of the type disclosed in the above U.S. Pat. No. 4,077,405.

The apparatus housing also includes a third chamber which contains a second bellows capsule which is mounted so that the interior of the second capsule communicates with the second chamber. In other words, the auxiliary capsule is basically a variable volume extension of the second chamber. The second capsule is smaller than the first capsule which is the main infusate reservoir and it is also biased toward its compressed condition by a two-phase fluid filling the space between the second capsule and the wall of the third chamber. However, the vapor pressure of the two-phase fluid on the second capsule is arranged so that it is less than the pressure of the two-phase fluid on the main capsule, but greater than the pressure at the infusion site.

After the apparatus is implanted in the body, its main bellows capsule is filled with infusate which operation recharges the vapor pressure power source for that main reservoir. Then the controller is directed to move the valve member against the second valve seat (stopping flow to the catheter) for a sufficiently long period of time to enable infusate expelled from the main capsule to completly fill the second chamber including the second bellows capsule. The extension of the second capsule thereupon recharges the vapor pressure power source that drives the second bellows capsule. Then, the pulses from the controller cease so that the valve member automatically moves back against the first valve seat stopping further flow of infusate from the main bellows capsule and opening the flow path to the catheter.

At this point, the two-phase fluid in the third chamber compresses the second bellows capsule so that infusate is expelled from the second chamber through the discharge tube and catheter to the infusion site. The infusate will continue to flow until the auxiliary capsule is fully compressed whereupon infusate flow stops until the solenoid is again energized by pulses from the controller to move the valve member to its second position permitting additional infusate to flow from the main bellows capsule into the second chamber and refill the second capsule. This process repeats itself until the supply of infusate in the main capsule is exhausted at which point the apparatus is refilled by injecting more infusate through the septum to refill the main bellows capsule.

Thus in the present infusion apparatus, the patient dosage is determined by the volume of the second bellows capsule and the cycle rate of the solenoid valve, rather than by the pressures of the two-phase fluids that drive the bellows capsules. Consequently the flow rate to the infusion site is substantially unaffected by changes in the pressures of the two-phase fluids due to changes in body temperature or ambient pressure.

Also it is a feature of this invention that if there is a failure of the valve or the controller in either of its two positions, the patient, under the worst circumstances, only receives a total dose equal to the volumetric change in the auxiliary bellows capsule as it moves between its fully extended and fully compressed positions. In other words, if the valve fails when the valve member is in its second position, there is no infusate flow from the second chamber to the infusion site. On the other hand if the valve fails when the member is in its first position, infusate will flow to the infusion site only until the auxiliary bellows capsule is fully compressed whereupon the infusate flow stops because the available fluid in the chamber has been exhausted and that chamber does not receive a new infusate supply from the main chamber. Of course, the volume of the auxiliary capsule is made sufficiently small that the infusate volume expelled by a single stroke of the second capsule constitutes a harmless dose.

Another advantage of the present infusion apparatus stems from the fact that all of the energy required to pump infusate from the apparatus is provided by the two-phase fluids which energy sources are automatically recharged each time the two bellows are refilled with infusate. Thus electrical energy is required only periodically and for a relatively short time when actuating the valve. Therefore the apparatus can operate on a continuous basis for a long period of time (e.g. several years) before its battery requires replacement or recharging. As a result of the aforesaid advantages, the present implantable infusion apparatus should find wide application as a dispenser for insulin, hormones and other such beneficial fluids.

BRIEF DESCRIPTION OF THE DRAWING

For a fuller understanding of the nature and objects of the invention, reference should be had to the following detailed description taken in connection with the accompanying drawing in which.

DESCRIPTION OF THE PREFERRED EMBODIMENT

Figure 1:
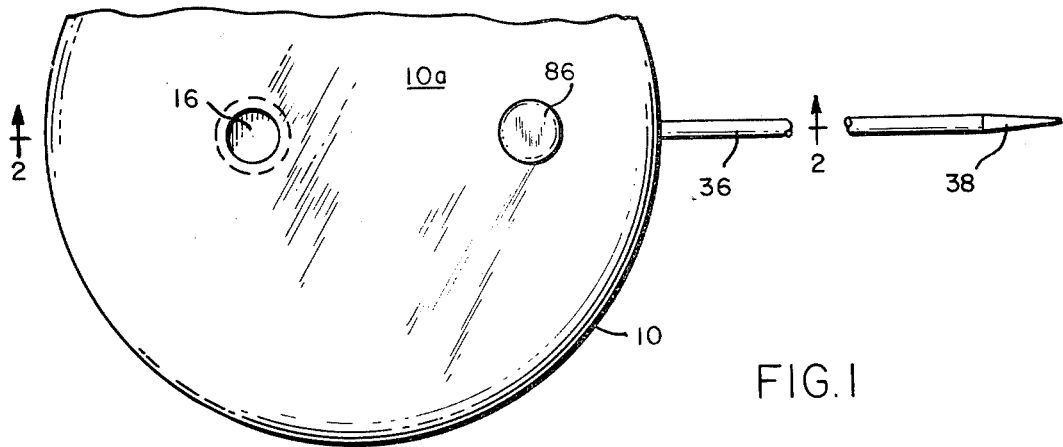
FIG. 1 is a top plan view of implantable infusion apparatus made in accordance with this invention.
Figure 2:
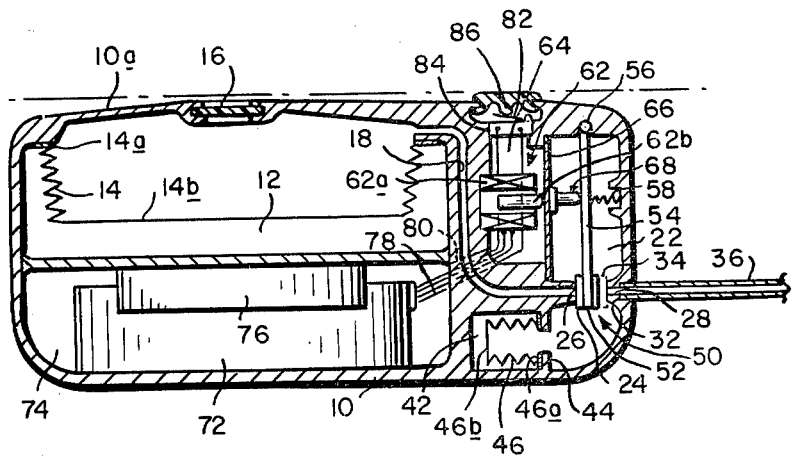
FIG. 2 is a sectional view along line 2—2 of FIG. 1.

Referring to FIGS. 1 and 2 of the drawing, the infusion apparatus comprises a generally cylindrical housing 10 whose interior is subdivided into several fluid-tight chambers or compartments. Mounted within a relatively large chamber 12 inside the housing is a large metal bellows capsule 14. One end 14a of the capsule is open and secured to the inner face of housing wall 10a. The opposite capsule ene 14b is closed. The capsule thus divides chamber 12 into two volumes, one being inside the capsule and the other being outside the capsule but within chamber 12. Furthermore, these volumes change in a reciprocal manner as the capsule is extended and compressed.

A penetrable self-sealing septum 16 is mounted in the housing wall 10a so that the bellows capsule 14 can be filled with infusate by injection through septum 16. Also the space in chamber 12 outside of the bellows is filled with a two-phase fluid such as chloroethane which tends to vaporize at body temperature thereby compressing capsule 14 and expelling infusate from the capsule. Thus capsule 14 and expelling infusate from the capsule. Thus capsule 14 and the confined two-phase fluid comprise a refillable vapor pressure pump of the type described in detail in the aforesaid patents.

A passage 18 extends from the bellows capsule 14 through an interior wall of the housing to a second chamber 22 within the housing. Also the end of passage 18 in chamber 22 is defined by a neck 24 that projects into chamber 22 and forms a valve seat 26 at the end of passage 18. A second passage 28 extends from chamber 22 through the outer wall of housing 10. The passage 28 end inside chamber 22 is defined by a projecting neck 32 located directly opposite neck 24 which forms a second valve seat 34 spaced directly opposite valve seat 26. Tube 36 has one end secured to the housing wall 10 in communication with passage 28, its opposite end being connected to a catheter 38 to be located at the infusion site in the body.

A third chamber 42 is located in the housing adjacent to chamber 22 and which has a relatively narrow mouth 44 that communicates with chamber 22. Situated inside chamber 42 is a second or auxiliary bellows capsule 46 having one end 46a which is open and secured at the chamber mouth 44, the opposite capsule end 46b being closed. Thus capsule 46 divides chamber 42 into two spaces one being inside the capsule 46 and the other being outside the capsule but within chamber 42. Furthermore, the volumes of those spaces vary reciprocally as the bellows 46 expands and contracts.

The space inside bellows 46 being in communication with chamber 22 is essentially, then, a variable volume extension of chamber 22. The space in chamber 42 outside of the bellows capsule is also filled with a two-phase fluid which vaporizes at body temperature and exerts a collapsing pressure on capsule 46. Consequently, the capsule 46 and its two-phase fluid constitute an auxiliary vapor pressure pump which functions more or less in the same way as the main infusate pump in chamber 12. However, the pressure of the two-phase fluid on capsule 46 is arranged to be less than the pressure of the two-phase fluid on capsule 14. Furthermore, the amount of fluid that it can pump during any given stroke is a small percentage of that pumped by a single stroke of bellows capsule 14.

As best seen in FIG. 2, valve means shown generally at 50 is located in chamber 22 for selectively opening and closing passages 18 and 28. The illustrated means 50 includes a single valve member 52 positioned directly between the valve seats 26 and 34. Member 52 is mounted on one end of a flexible resilient reed 54 whose opposite end is secured at 56 to the inside surface of the housing wall 10a. Thus the valve member can be moved to seat alternatively on valve seat 26 or valve seat 34. When the member is seated on valve seat 26, the end of passage 18 is closed so that no fluid can flow from capsule 14 into chamber 22. However, fluid can flow from chamber 22 through passage 28 to catheter 38. On the other hand when the valve member is in its opposite position wherein it seats on valve seat 34, fluid is free to flow from capsule 14 through passage 18 into chamber 22. However, passage 28 being closed, no fluid can flow from chamber 22 to the catheter.

Means such as a spring 58 is compressed between reed 54 and the side wall 10b of the housing so as to bias the reed 54 inwardly so that the valve member 52 is normally seated on valve seat 26 thereby closing passage 18 so that no fluid can flow from the bellows capsule 14 into chamber 22. Alternatively, the valve reed itself may provide the bias. The valve member is moved to its opposite position wherein it seats on valve seat 34 by the actuator illustrated here as a solenoid assembly indicated generally at 62 mounted in a compartment 64 inside the housing adjacent chamber 22. The actuator could, however, be magnetic or piezoelectric. The compartment and chamber share a common wall in the form of a flexible resilient diaphragm which isolates those two spaces. Compartment 64 could also be filled with the two phase fluid to produce a pressure balance and reduce the power required to move diaphragm 66.

The solenoid assembly includes a winding 62a whose axis is oriented perpendicular to that of reed 54 and an armature 62b whose free end is secured to one side of diaphragm 66. Fastened to the opposite side of diaphragm 66 directly opposite armature 62b is a pin 68 whose free end engages reed 54. When the solenoid winding is de-energized, the spring 58 biases the reed 54 so that the valve member 52 seats on valve seat 26. On the other hand when the solenoid winding is energized, the armature 62b is thrust outward thereby flexing reed 54 and unseating the valve member 52 from valve seat 26 and seating that member against valve seat 34.

The solenoid assembly 62 is energized by electrical pulses from a controller 72 positioned in another compartment 74. The controller 72 receives its energy from a battery 76 located in that same compartment. Electrical connections from the controller to the solenoid are made by electrical leads 78 extending through a feedthrough 80 in an interior wall of the housing. Controller 72 is a programmable device that issues pulses of a selected duration and/or repetition rate to control the position of the valve member 52. An example of a suitable controller is disclosed in the aforesaid U.S. Pat. No. 4,077,405 and hence it will not be detailed here.

Also as is commonly found in apparatus of this type, a manual switch 82 may be mounted in a recess 84 in housing wall 10a, the mouth of the recess being closed by membrane 86 installed in housing wall 10a. The switch is connected between the solenoid and the battery in parallel with the controller so that depression of the switch energizes the solenoid so long as the switch remains depressed.

When the apparatus is implanted in the body, both the septum 16 and the membrane 86 are situated directly under the skin so that the apparatus can be refilled by injection of infusate through the skin and through the septum 16 and it can be operated manually by depressing the skin area which overlies membrane 86.

It should be understood that for purposes of this description we have omitted the various filters, internal flow restricters and other details normally found in implantable infusion apparatus of this general type because those elements are not necessary for a complete description of the present invention. As a matter of interest, those details are fully disclosed in the aforesaid patents.

In describing the operation of the present apparatus, we will assume that it is properly implanted in the body and that the main bellows capsule 14 is completely filled with infusate. The two-phase fluid in chamber 12 vaporizes at body temperature and exerts a force tending to compress the bellows capsule 14. However no infusate can flow into chamber 22 because the valve member 52 is seated on valve seat 26 blocking that passage as shown in solid lines in FIG. 2. The valve member is now moved to its second position on seat 34 shown in dotted lines in FIG. 2, to initially fill chamber 22 with infusate. This may be done either by depressing the manual switch 82 or by programming controller 72 to issue a pulse to solenoid assembly 62 so that infusate flows continuously from capsule 14 until the chamber 22 and auxiliary capsule 46 are filled. Of course, during this time, the valve member 52 being seated on valve seat 34 prevents infusate flow to the catheter 38.

When chamber 22 and capsule 46 are filled with infusate, the solenoid is de-energized so that member 52 returns to its normal position against valve seat 26 shutting off further flow of infusate from the main bellows capsule 14 and opening passage 28 leading from chamber 22. At this point, the two-phase fluid in chamber 42 having been compressed by extension of auxiliary bellows capsule 46 exerts a force tending to compress that capsule thereby forcing infusate from chamber 22 through passage 28 to catheter 38. The apparatus continues to dispense infusate until bellows capsule 46 has moved its fully compressed position whereupon flow of infusate to catheter 38 stops because there is no force remaining to pump it from chamber 22.

If now, the solenoid assembly 62 is again energized by a pulse from controller 72 or because of the depression of the switch 82, the valve member 52 again moves away from valve seat 26 so that additional infusate is pumped from capsule 14 into chamber 22. As stated previously, the pressure of the two-phase fluid in chamber 12 on capsule 14 is greater than the pressure of the two-phase fluid in chamber 42 on bellows capsule 46. Consequently, any flow of infusate into chamber 22 is able to extend capsule 46 thereby essentially refilling and recharging that auxiliary pump. As soon as the solenoid 62 is de-energized, valve member 52 reseats on valve seat 26 and infusate again commences to flow through outlet passage 28 to catheter 38.

It is apparent from the foregoing that if the discharge volume of the auxiliary bellows capsule 46 is relatively small compared to that of the main capsule 14, the infusate dosage that a patient receives during a given period of time is determined substantially by the volume of capsule 46 and the cycle rate of valve 50. In a typical example, the main capsule 14 might contain a month's supply of infusate. In other words it is refilled monthly by injection through septum 16. On the other hand, auxiliary capsule 46 might discharge only a five minute supply of infusate during each stroke. Therefore, to maintain the basal flow rate, controller 72 issues a pulse to solenoid 62 every five minutes to refill capsule 46 which then immediately discharges its contents into the patient. Then, to provide the bolus dose, after each meal for the diabetic patient, say, at 8, 12 and 18 hundred hours the controller issues several pulses to the solenoid 62 so that capsule 46 is refilled from the main capsule several (e.g. five or ten) times during a relatively short time period discharging five or ten times the basal dosage into the patient during that period.

It is apparent from the foregoing then that the long term basal dosage to the patient is maintained to an accuracy of five minutes or less which is thought by the medical profession to be a desirable tolerance. Further, since the basal dosage is set by the volume of capsule 46 and the valve cycle rate, a small orifice outlet flow restriction is not required for that purpose with its attendant problems of difficulty of manufacture and proneness to blockage discussed above.

Still, however, since a single stroke of capsule 46 provides the basal flow for a full five minutes, the valve solenoid 62 needs only to receive a pulse at five minute intervals so that its duty cycle is short and its power requirements low compared to prior devices which are pulsed more or less continuously. Therefore, battery 76 should last for a long time before requiring recharging or replacement.

This also means that the flow of infusate to the patient is substantially unaffected by changes in the pressure of the two-phase fluids on bellows capsules 14 and 46 as might be caused for example by temperature changes in the body. That is, even if the patient has a temperature causing capsule 46 to discharge all its infusate in one minute, it still will not be refilled until four more minutes elapse when controller 72 issues the next pulse. Consequently, there is no need in the present apparatus to monitor the pressure of the two-phase fluids to compensate for such temperature or pressure induced variations.

Also, there is little danger of the patient receiving an overdose of infusate due to malfunction of the valve 50. This is because if the valve member 52 becomes locked in either of its two positions, the patient receives little or no infusate. That is, if valve member 52 locks on its solid line position in FIG. 2, no infusate can flow from the bellows capsule 14 into chamber 22. Therefore, infusate will flow from chamber 22 to catheter 38 only until the auxiliary bellows capsule 46 assumes its fully compressed position whereupon infusate flow immediately stops. As noted above, the volume of capsule 46 is such that only a minimal dosage of infusate is pumped out of the apparatus for each stroke of that bellows capsule. On the other hand, if valve member 52 fails in its dotted line position shown in FIG. 2, no infusate at all will flow from chamber 22 to the catheter because outlet passage 28 is closed.

Since the present infusion apparatus relies totally on the two-phase fluids to achieve its pumping action, it only requires the energy from its battery 76 to periodically pulse the solenoid 26. Therefore the apparatus can operate uninter-ruptedly for a prolonged period of time without having to replace the battery.

It will thus be seen that the objects set forth above, among those made apparent from the preceding description, are efficiently attained. Also certain changes may be made in the above construction without departing from the scope of the invention. For example, the capsules 14 and 46 can be moved by a gas such as Freon or an actuator, piston or other such motive means instead of the two phase fluids. Therefore, it is intended that all matter contained in the above description or shown in the accompanying drawing be interpreted as illustrative and not in a limiting sense.

It is also be be understood that the following claims are intended to cover all of the generic and specific features of the invention herein described.

I claim:
1. Implantable infusion apparatus comprising
    A. a housing,
    B. a variable volume main infusate reservoir positioned in the housing,
    C. a variable volume auxiliary infusate reservoir positioned in the housing, said auxiliary reservoir having a smaller volume than said main reservoir,
    D. a first fluid passage communicating between the main reservoir and the auxiliary reservoir,
    E. a second fluid passage communicating from the auxiliary reservoir exteriorly of said housing,
    F. valve means mounted inside the housing, said valve means being movable between a first position that opens said first passage while closing the second passage and a second position that closes the first passage while opening the second passage,
    G. a confined fluid under pressure acting on the main reservoir tending to reduce its volume and thereby pressurize the infusate therein to a first pressure,
    H. a confined fluid under pressure acting on the auxiliary reservoir tending to reduce its volume and thereby pressurize the infusate therein to a second pressure less than the first pressure so that
        (1) when the valve means is in its said first position, infusate flows from the main reservoir to the auxiliary reservoir whereupon, due solely to the higher pressure of the infusate in the main reservoir, the auxiliary reservoir volume is enlarged thereby raising the pressure of the confined fluid acting on that reservoir, and
        (2) when the valve is in its second position, infusate flows from the auxiliary reservoir through the second fluid passage whereupon, due solely to the raised pressure of the confined fluid acting on the auxiliary reservoir, the volume of the auxiliary reservoir is reduced thereby forcing infusate from the auxiliary reservoir through the second fluid passage, and
    I. means for moving the valve means between its two positions.

2. The infusion apparatus defined in claim 1 wherein each said force exerting means comprises an enclosed volume of a two-phase fluid exposed to a reservoir and which exerts a vapor pressure tending to compress said reservoir at body temperatures.

3. The infusion apparatus defined in claim 1 wherein the valve moving means comprises
    A. means for biasing the valve means so that said first passage is closed and said second passage is open,
    B. solenoid actuator means arranged to move the valve means so that said valve means open said first passage and close said second passage when solenoid actuator means is energized, and
    C. means for energizing the solenoid actuator means at selected times.

4. The infusion apparatus defined in claim 3 wherein the energizing means comprises
    A. a battery, and
    B. means for selectively connecting the battery in circuit with the solenoid actuator means.

5. The infusion apparatus defined in claim 4 wherein the connecting means comprises a programmable controller.

6. The infusion apparatus defined in claim 4 wherein the connecting means comprises a switch operable from without said housing.

7. The infusion apparatus defined in claim 1 and further including means including a penetrable septum in a wall of said housing to facilitate refilling of said main reservoir with infusate.

8. The infusion apparatus defined in claim 1 wherein said valve means includes a single, two-position valve member which opens and closes both said first and second passages in a reciprocal fashion so that if the valve member remains in one position for a prolonged period infusate can flow through the second passage and if it remains in its other position for a prolonged period, only an infusate volume corresponding to the discharge volume of the auxiliary capsule can flow through the second passage.

9. The infusion apparatus defined in claim 1 wherein the valve moving means comprises
    A. means for biasing the valve means toward its said first position, and
    B. means operable from outside the housing for moving the valve means from its said first position to its said second position.

* * * * *

UNITED STATES PATENT AND TRADEMARK OFFICE
CERTIFICATE OF CORRECTION

PATENT NO. : 4,221,219

DATED : September 9, 1980

INVENTOR(S) : Elton M. Tucker

It is certified that error appears in the above-identified patent and that said Letters Patent are hereby corrected as shown below:

Col. 3, Line 8, change "caridac" to --cardiac--.

Col. 4, Line 25, change "completly" to --completely--.

Col. 5, Line 40, change "ene" to --end--.

Col. 5, Line 53, delete all between "capsule" (first occurrence) and "the".

Col. 8, Line 3, change "its" to --to its--.

Col. 9, Line 7, change "on" to --in--.

Col. 9, Line 25, change "uninter-ruptedly" to --uninterruptedly--.

Col. 10, Line 53, before "infusate", insert --no--.

Signed and Sealed this

Ninth Day of December 1980

[SEAL]

Attest:

Attesting Officer

SIDNEY A. DIAMOND

Commissioner of Patents and Trademarks